United States Patent [19]

DiMassimo et al.

[11] Patent Number: 4,805,626
[45] Date of Patent: Feb. 21, 1989

[54] AIR FLOTATION PATIENT BED

[75] Inventors: Virgil DiMassimo, Huntington Station; Mark J. Gelbien, Levittown, both of N.Y.

[73] Assignee: Fonar Corporation, Melville, N.Y.

[21] Appl. No.: 935,207

[22] Filed: Nov. 26, 1986

[51] Int. Cl.$^4$ ............................................... A61B 5/05
[52] U.S. Cl. ................................... 128/653; 269/322; 269/20; 406/86
[58] Field of Search ............... 128/653, 714; 5/81 B; 269/322, 20; 198/750, 811; 406/86–88; 378/209

[56] References Cited

U.S. PATENT DOCUMENTS

| | | | |
|---|---|---|---|
| 3,417,878 | 12/1968 | Schonfelder et al. | 406/88 |
| 3,481,324 | 12/1969 | Talbot et al. | 128/714 |
| 3,941,238 | 3/1976 | Lapeyre | 198/811 |
| 3,944,204 | 3/1976 | Cesar | 378/209 |
| 4,071,137 | 1/1978 | Fink | 198/955 |
| 4,444,541 | 4/1984 | Bergman | 269/20 |
| 4,574,705 | 3/1986 | Von Winckelmann | 406/86 |
| 4,615,042 | 9/1986 | Schmedemann | 269/322 |
| 4,616,960 | 10/1986 | Gladish | 198/811 |

*Primary Examiner*—Ruth S. Smith
*Attorney, Agent, or Firm*—Lerner, David, Littenberg, Krumholz & Mentlik

[57] ABSTRACT

A patient bed for use with an NMR scanner utilizes a surface extending into the RF coil having a plurality of valves projecting therefrom which vent pressurized air when depressed. A patient bed, disposed over the surface, depresses the valves therebelow, engendering a cushion of air under the bed. The bed is selectively positioned in and out of the examination region via a sprocket-driven perforated belt which engages a sprocket on the bed. In a second embodiment, the bed is supported by a cushion of air on a vertically adjustable pedestal which is placed adjacent an NMR scanner which also provides a cushion of air for supporting the bed which is moved from the pedestal to the scanner and thereafter returned to the pedestal. Methods in accordance with the apparatus of the present invention are also disclosed.

31 Claims, 3 Drawing Sheets

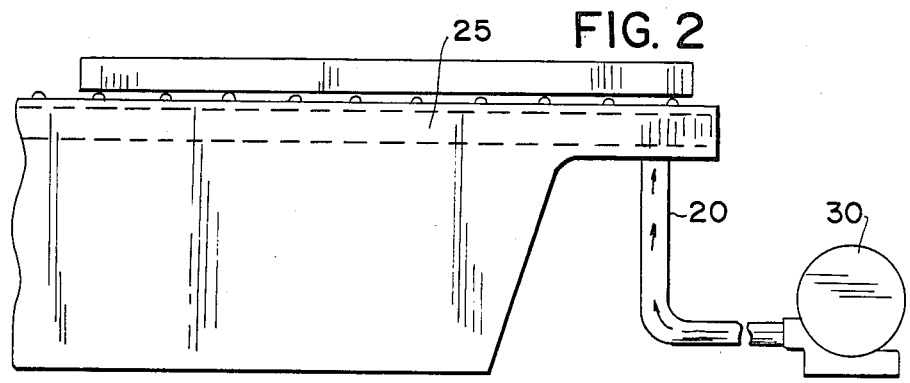
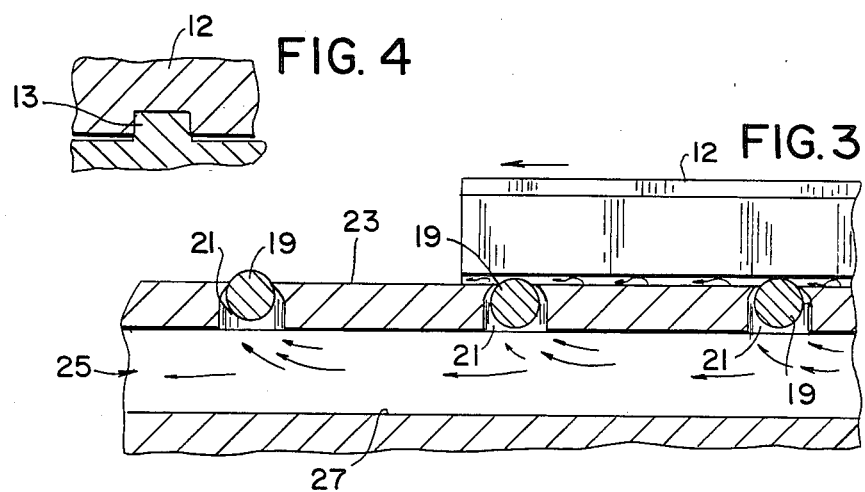
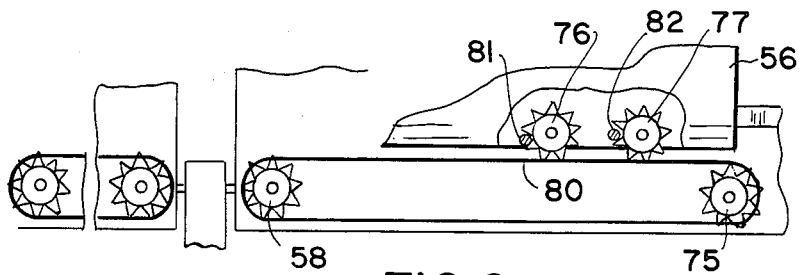

AIR FLOTATION PATIENT BED

FIELD OF THE INVENTION

The present invention relates generally to patient beds, and more particularly, to patient beds which are positionable in NMR scanners via air flotation.

BACKGROUND OF THE INVENTION

NMR scanner apparatus are utilized in the medical domain for providing images of selected portions of a patient's anatomy. These images are helpful in ascertaining the health of the patient. According to the prior art, to position the patient in the NMR scanner, a bed is utilized generally having wheels which are guided by tracks that run through the scanner. In this fashion, a patient may be positioned in the scanner by placing the patient on the bed, moving the bed along the tracks into the scanner, and when the examination is completed, moving the bed along the tracks out of the scanner to remove the patient therefrom. Owing to the character of the NMR scanner, the patient bed, including the wheels must be free of all metal that would otherwise affect the operation of the scanner. Thus, the wheels of the prior art patient beds are nonmetallic, and generally composed of nylon or the like. Under the weight of the patient, these nonmetallic wheels tend to deform, and thereby resist movement of the patient bed. That is, the patient beds of the prior art utilized in conjunction with NMR scanners are difficult to position owing to the necessity of utilizing nonmetallic wheels which inhibit movement of the bed when their circular shapes are distorted by the weight of the patient which they bear. Thus, the beds of the prior art utilized in conjunction with NMR scanners entail significant problems in easily and quickly positioning a patient relative to the scanner.

Thus, there is a need for an apparatus containing no metallic components, which can facilely and readily install a patient into, and withdraw a patient from an NMR scanner.

SUMMARY OF THE INVENTION

The present invention entails a method and apparatus for selectively positioning an object in an examination region of an examination apparatus.

A first embodiment of an apparatus in accordance with the present invention includes means for examining an object. The examination means possesses a region into which the object is placed for examination purposes. The apparatus further includes means for transporting the object; and means, coupled to the examining means, for supporting the transporting means with air so that the transporting means with the object may be selectively positioned in and out of the examination region. The transporting means is situated on the supporting means.

In a preferred embodiment of the above-described apparatus, the means for examining an object comprises an NMR scanner, and the transporting means comprises a patient bed. The supporting means comprises a surface extending to the examination region of the NMR scanner, and valves distributed along and projecting from the surface. The valves are designed to open when the patient bed passes thereover, and to close otherwise. The supporting means further comprises tracks disposed along the surface which extend from the examination region. The valves are situated between the tracks. The bottom surface of the patient bed contains grooves which engage the tracks. This preferred embodiment further includes two sprockets, spaced apart, situated along the surface which extends into the examination region. A belt, having perforations therein, is disposed around and cooperates with the two sprockets. A third sprocket is rotatably fixed to the side of the patient bed in engagement with the belt. A device, such as a pin disposed between teeth of the third sprocket, is utilized to selectively permit the third sprocket to rotate. With the pin inserted between the teeth of the third sprocket, the bed may be selectively positioned by pumping pressurized air into the valves, and by driving one of the sprockets with a motor, thereby moving the belt. In this fashion, the patient bed with the patient thereupon is supported by a cushion of air therebelow, and may be selectively positioned in the examination region and, when the examination has been completed, removed therefrom. Should the belt which engages the third sprocket fail to move, for whatever reason, the patient bed supported by the cushion of air may be manually positioned by releasing the pin, thereby freeing the third sprocket to rotate. The patient bed is then free to be moved along the immobile belt.

A second apparatus in accordance with the present invention includes means for examining an object; and a pedestal disposed adjacent the examining means. Further, this apparatus includes means, situated on the pedestal, or transporting the object. The pedestal includes first means for supporting the transporting means with air so that the transporting means with the object may be selectively positioned. The means for examining the object includes a region in which the object is situated for examination, and second means for supporting the transporting means with air so that the transporting means with the object may be selectively positioned in and out of the examination region.

In a preferred embodiment of the second apparatus of the present invention, the examining means comprises an NMR scanner, and the transporting means comprises a patient bed. The first supporting means comprises a horizontal surface of the pedestal having valves projecting therefrom. The valves are designed so that they open when the patient bed passes thereover and close otherwise. Air may be pumped beneath this horizontal surface of the pedestal. The first supporting means further includes tracks disposed along the horizontal surface such that the valves are situated therebetween. The patient bed possesses a lower surface having grooves therein which engage the tracks. The second supporting means comprises a surface extending to the examination region of the NMR scanner, having valves projecting therefrom. These valves are also designed to open when the patient bed passes thereover and to close otherwise. Air may be pumped beneath this surface. Further, tracks are disposed along this surface such that the valves are situated therebetween. These tracks are configured to cooperate with the grooves on the bed. A belt, disposed around two sprockets situated on the pedestal, engages two sprockets rotatably fixed to the patient bed. A second belt is disposed on the NMR scanner alone one of the tracks, around two sprockets affixed to the scanner. Both the belt on the pedestal and that on the scanner are driven in synchronism by a single motor. As for the first embodiment, pins or other such devices are utilized to prevent rotation of the sprockets on the patient bed. To selectively position the patient bed in the NMR scanner, pressurized air is pumped to the valves on the pedestal, lifting the bed, and to the valves on the scanner. Also, the motor is energized to drive the belt on the pedestal, moving the patient bed across the gap between the pedestal and the NMR scanner, onto the NMR scanner. At this point, the moving belt on the NMR scanner engages the nearest sprocket on the patient bed, pulling the bed towards the NMR scanner and into the examination region. The bed is supported on the scanner by a cushion of air therebeneath. After the bed is selectively positioned, the motor is deactivated and the pressurized air is eliminated. When an examination has been completed, the patient bed may be withdrawn from the NMR scanner by, once again, applying pressurized air to the valves on the scanner and pedestal, and by activating the motor to reverse the motion of the belt on the NMR scanner, and the belt on the pedestal. Should either of these belts fail to move, the pins or other such devices preventing rotation of the sprockets on the patient bed may be released, thereby permitting the patient bed to be manually positioned along the immobile belts.

The present invention also entails a method of selectively positioning an object in an examination apparatus having an examination region and a surface extending to the region. This method includes disposing a support on the surface which extends into the examination region, and placing an object for examination on the support. The support is cushioned with air so that the support with the object may be selectively positioned relative to the examination region. The support with the object thereupon is then selectively positioned relative to the region.

In a preferred embodiment of this method, the examination apparatus is an NMR scanner, and the support is a patient bed.

The present invention also entails a second method of selectively positioning an object in an examination apparatus having an examination region and a surface extending thereto. This method comprises positioning a pedestal adjacent to the examination apparatus, and placing a support on the pedestal. The object is placed on the support. The support is cushioned with air so that the support with the object thereupon may be moved towards the examination apparatus. This method further entails providing for a cushion of air on the surface extending into the examination region. The support is then selectively positioned relative to the examination region.

In a preferred embodiment of this second method, the examination apparatus is an NMR scanner, and the support is a patient bed.

The present invention permits accurate and facile positioning of a patient into and out of the examination region of an NMR scanner. Unlike the prior art, the present invention entails no wheels which may deform and thereby create problems in moving the patient relative to the scanner. The present invention entails no metallic components and, accordingly, does not impair the operation of the scanner.

Thus, the present invention overcomes the difficulties associated with the prior art in positioning patients in and out of NMR scanners, and simultaneously provides a simple, reliable and easy means of so doing.

BRIEF DESCRIPTION OF THE DRAWINGS

FIG. 2 is a fragmentary, side elevational view of the first preferred embodiment of the present invention depicted in FIG. 1.

FIG. 3 is a fragmentary, vertical sectional view of the first preferred embodiment depicted in FIG. 1, illustrating the operation thereof.

FIG. 4 is a fragmentary, vertical sectional view of the first preferred embodiment depicted in FIG. 1, illustrating a guide rail and a patient bed disposed thereon.

FIG. 6 is a fragmentary, partially broken away, top plan view of the second preferred embodiment of the present invention depicted in FIG. 5.

Identical numerals in different figures refer to identical elements.

DETAILED DESCRIPTION OF THE PREFERRED EMBODIMENTS

The present invention entails a method and apparatus for moving a patient into and out of an NMR scanner without impairing the operation thereof.

Figure 1:
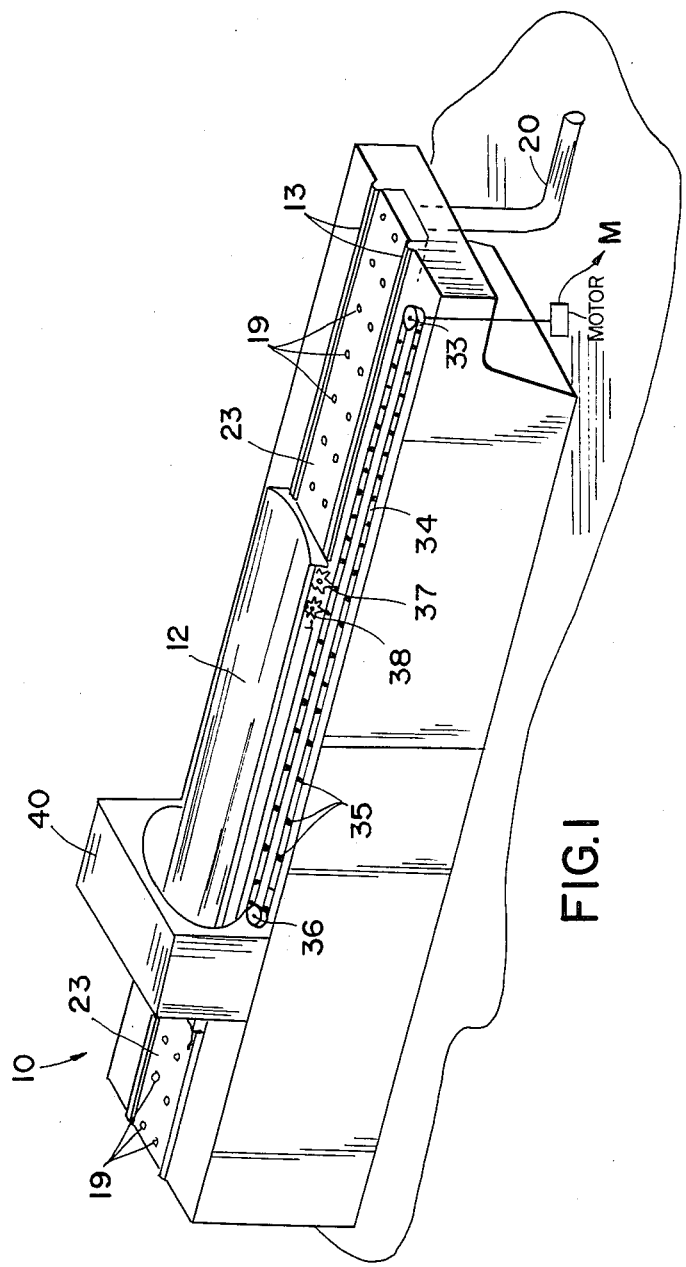
FIG. 1 is a perspective view of a first preferred embodiment according to the present invention.

Referring to FIGS. 1 and 4, a patient bed 12 is supported on tracks 13, which are disposed on an NMR scanner subassembly, generally designated 10. The bed 12 can be positioned along the tracks 13. Referring also to FIG. 3, a plurality of spheres 19 are disposed in corresponding openings 21 in an upper surface 23 of the scanner subassembly 10. Preferably, the tracks 13, the openings 21 and the corresponding spheres 19 are not disposed along the portion of the surface 23 which extends into an RF coil 40 of the scanner subassembly 10. Indeed, the surface 23 need not extend into the RF coil; there may be an opening at the base of the coil 40. A chamber 25 is disposed between the upper surface 23 and a lower surface 27. Referring also to FIG. 2, a pump 30 forces air, via a conduit 20, into the chamber 25. The openings 21 are restricted at their upper ends so that the spheres 19, when forced upwardly by the pressure of the air in the chamber 25, fit tightly therein, thereby preventing escape of the air in the chamber 25. Further, referring specifically to FIG. 3, the patient bed 12 is disposed so that the spheres 19 which lie thereunder are depressed in the openings 21, thereby permitting air in the chamber 25 to escape from the upper ends of the openings 21 which lie beneath the patient bed 12. In this fashion, the air being forced into the chamber 25 by the pump 30, via the conduit 20, escapes only from the openings 21 immediately beneath the patient bed 12, thereby lifting the patient bed 12 upwardly. Accordingly, the patient bed 12 is easily positioned along the tracks 13. Since the air in the chamber 25 escapes only from the openings 21 disposed immediately beneath the patient bed 12, the full force and cushioning effect of the air is concentrated on the patient bed 12. That is, the force of the air in the chamber 25 is not dissipated by air escaping from the openings 21 which are not below the patient bed 12, and thus, the force is vented only under the patient bed 12. The full force of the air in the chamber 25 is applied, accordingly, only in lifting the patient bed 12.

With the reduction in friction of the patient bed 12 on the tracks 13, it is possible to manually slide a patient on the bed 12 into and out of the RF coil 40 of the NMR scanner subassembly 10. However, referring to FIG. 1, means may be employed to facilitate the positioning of the patient bed 12 along the tracks 13. A sprocket 33, driven by a motor M, drives a sprocket 36 via a belt 34 having perforations 35. A sprocket 38 and a sprocket 37 are rotatably fixed to the foot end of the patient bed 12, and mate with the perforations 35 of the belt 34. Each of the sprockets 37 and 38 is prevented from rotating by a pin, lever, latch or similar mechanism, which may be released to permit rotation.

Referring to FIGS. 1 and 2, in operation, with the patient bed 12 withdrawn from the RF coil 40 of the NMR scanner subassembly 10, a patient is placed on the bed 12. The sprockets 37 and 38 are prevented from rotating via one of the mechanisms described above. The air pump 30 is turned on to provide a cushion of air beneath the bed 12, and a motor (not shown) is turned on to drive the sprocket 33 to push, via the belt 34, the bed 12 into the RF coil 40. When the bed 12 with the patient thereupon is properly positioned in the RF coil 40, the motor driving the sprocket 33 is switched off, and the air pump 30 is also deactivated. The bed 12 then settles on the tracks 13, in frictional contact therewith. The patient is then scanned. To scan another portion of the patient, the motor driving the sprocket 33, and the pump 30 are activated, and the bed 12 is repositioned. The motor and the pump 30 are then deactivated, allowing the bed 12 to settle on the tracks 13, and a second scan is taken of the patient. This procedure may be repeated for any selected number of positions corresponding to portions of the patient desired to be scanned. In accordance with NMR techniques, the present invention, in particular, permits the patient to be moved three inches at a time, quickly through the Rf coil 40, in order to sequentially scan various portions of the body. Of course, as indicated above, the present invention is not restricted to this mode of operation; any desired positioning of the patient bed 12 is possible. After scannining of the patient has been completed, the bed 12 may be withdrawn from the RF coil 40 by activating the air pump 30 which provides a cushion of air beneath the bed 12, and by activating the motor to drive the sprocket 33 in the opposite direction. In this fashion, the bed 12 is pulled, via the belt 34, away from the RF coil 40. When the bed 12, with the patient thereupon, is withdrawn from the RF coil 40 to a desired point, the motor driving the sprocket 33 is deactivated, and the air pump 30 is also deactivated.

In this fashion, a patient may be effortlessly and quickly moved into, through, and out of the Rf coil 40 of the NMR scanner subassembly 10. The cushion of air provided beneath the patient bed 12 greatly reduces the friction between it and the tracks 13, thereby permitting a motor having relatively low horsepower to move the bed 12. Should the belt 34 cease moving due to a failure of the motor, the bed 12 may be positioned manually by releasing the pins or other mechanisms which prevent the sprockets 37 and 38 from rotating. With the sprockets 37 and 38 free to rotate, the bed 12 may be easily pushed or pulled along the belt 34, owing to the cushion of air therebeneath.

Figure 5:
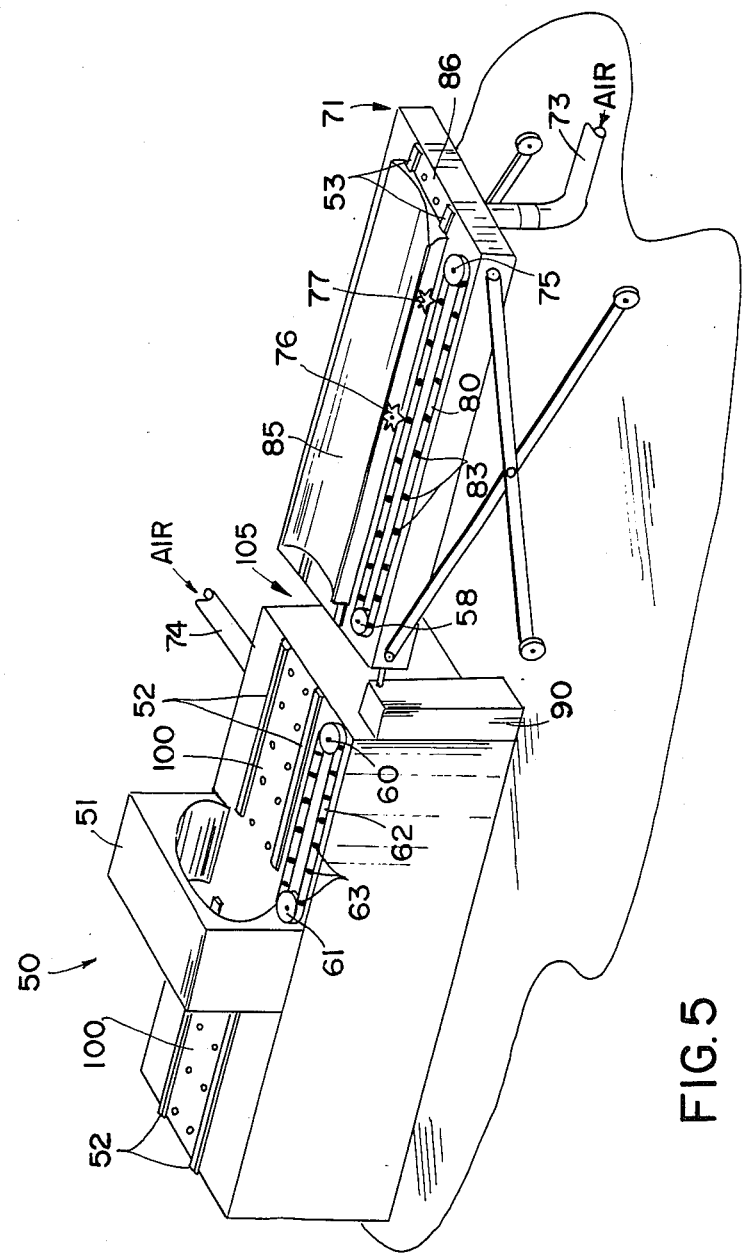
FIG. 5 is a perspective view of a second preferred embodiment in accordance with the present invention.

Referring to FIGS. 5 and 6, a second embodiment of the present invention is depicted. A patient bed 85 is supported on a vertically adjustable pedestal generally designated 71, which is disposed adjacent an NMR scanner subassembly 50. Any means including manual and motor operated, may be utilized to vertically adjust the pedestal 71; the invention is not restricted to the use of cross-legs. A gap 105, exaggerated for clarity, may be disposed between the pedestal 71 and the scanner subassembly 50. The gap 105 may be adjusted to suit the situation. The bed 85 is disposed to move along tracks 53. A surface 86, disposed between the tracks 53 contains openings having spheres disposed therein similar to the openings 21 and the corresponding spheres 19 depicted in FIG. 3. As in the first embodiment, air is pumped into a chamber beneath the surface 86 via a conduit 73. The spheres in the openings immediately beneath the bed 85 are depressed by the bed 85, thereby permitting air to escape from these openings, providing support for the bed 85. A sprocket 76 and a sprocket 77 are rotatably fixed to the foot of the bed 85, and may be prevented from rotating by devices such as a pin 81 removably disposed between teeth of the sprocket 76, and a pin 82 removably disposed between teeth of the sprocket 77. The sprockets 76 and 77 mate with a belt 80 having perforations 83 therein. The belt 80 is disposed around a sprocket 75, and a sprocket 58 which is driven by a motor 90. The pedestal 71 is vertically adjustable to accommodate the height of the NMR scanner subassembly 50. The scanner subassembly 50 comprises an RF coil 51 and tracks 52 extending from the RF coil 51. As in the first embodiment, a surface 100, disposed between the tracks 52, and extending into the RF coil 51, includes a plurality of openings having spheres therein such as the openings 21 and the corresponding spheres 19 of FIG. 3. Preferably, the tracks 52, and the openings and the corresponding spheres are not disposed along the portion of the surface 100 which extends into the RF coil 51. Indeed, the surface 100 may not extend into the coil 51; there may be an opening at the base of the coil 51. Also, as in the first embodiment, air is pumped into a chamber beneath the surface 100 via a conduit 74. In response to the air pressure, the spheres in the openings in the surface 100 move upwardly preventing escape of air therefrom, until depressed by the passage of the bed 85 thereover. A belt 62 having perforations 63 therein configured for mating with the sprockets 76 and 77 is disposed around a sprocket 61, and around a sprocket 60 which is driven by the motor 90.

In operation, the pedestal 71 is vertically adjusted so that a patient may be placed on the bed 85. The height of the pedestal 71 is then matched with that of the NMR scanner subassembly 50. To position the bed 85 with the patient thereupon in the RF coil 51 of the NMR scanner subassembly 50, air is pumped into the conduit 73, and into the conduit 74. Accordingly, the bed 85 is supported on the pedestal 71 by a cushion of air thereunder. The motor 90 is activated to drive the sprocket 58 so as to move the bed 85, via the belt 80, towards the RF coil 51. The motor 90, which may be disposed in any convenient location, also simultaneously drives the sprocket 60 on the NMR scanner subassembly 50. With the pedestal 71 disposed so that the tracks 53 are aligned with the tracks 52, the bed 85 is pushed across the gap 105 towards the RF coil 51 by the belt 80 until the sprocket 76 engages the belt 62 on the NMR scanner subassembly 50. At this point, the belt 62, driven by the sprocket 60, pulls the bed 85 towards the RF coil 51. The spacing between the sprockets 76 and 77 is exaggerated, in accordance with the exaggeration of the gap 105. Shortly after the belt 62 engages the sprocket 76, it also engages the sprocket 77. In this fashion, the patient bed 85 is first pushed by the belt 80 towards the RF coil 51, and after crossing the gap 105 between the pedestal 71 and the NMR scanner subassembly 50 is pulled by the belt 62 into the RF coil 51. The movements of the belts 62 and 80, and the dispositions of their respective perforations 63 and 83 are predetermined so that the belts 62 and 80 are moving in synchronism and in phase. That is, owing to preliminary calibrations, the sprocket 76 engages the belt 62 while the sprocket 77 is engaged with the belt 80, without tearing or ripping of either the belt 62 or the belt 80. When the bed 85 bearing the patient thereupon is properly positioned in the RF coil 51, the motor 90 is deenergized, and the air being supplied via the conduits 74 and 73 is eliminated. The bed 85 then settles on the tracks 52, in frictional contact therewith. The patient is then scanned. To scan another portion of the patient, the motor 90 is activated, air is pumped under pressure into the conduit 74 to provide a cushion beneath the bed 85, and the bed 85 is repositioned. The motor 90 is then deactivated, the flow of pressurized air through the conduit 74 is eliminated, and a second scan is taken of the patient. This procedure may be repeated for any selected number of positions corresponding to portions of the patient desired to be scanned. As for the first embodiment, the second embodiment of the present invention, in particular, permits the patient to be moved three inches at a time, quickly through the RF coil 51, in accordance with NMR techniques, to sequentially scan various portions of the body. Of course, the second embodiment is not restricted to this mode of operation; any desired positioning of the patient bed 85 is possible. After scanning of the patient is completed, the bed 85 is withdrawn from the RF coil 51 by once again activating the motor 90 to drive each of the sprockets 58 and 60 in a direction opposite to its previous direction. Further, air is once again forced into the conduits 73 and 74, thereby providing a cushion of air beneath the bed 85 as it is moved. The belt 62 pulls the bed 85 from the RF coil 51 across the gap 105, until the sprocket 77 engages the belt 80. At this point, the belt 80 also pulls the bed 85 along the tracks 53 of the pedestal 71. Shortly after the belt 80 engages the sprocket 77, it also engages the sprocket 76. When the bed 85 with the patient thereupon has been withdrawn from the RF coil 51 to a desired position on the pedestal 71, the motor 90 is deactivated and the air supply to the conduits 73 and 74 is terminated. The patient may now be removed from the bed 85, before or after additional vertical adjustment of the pedestal 71.

If, at any time, the motor 90 fails, preventing movement of the belts 62 and 80, the bed 85 may be manually moved along the tracks 52 and 53 by releasing the pins 81 and 82 or other such devices from, respectively, the sprockets 76 and 77 to permit the sprockets 76 and 77 to rotate. In this fashion, with the belts 62 and 80 immobilized, and the sprockets 76 and 77 free to rotate, the bed 85 may be pushed along the tracks 52 and 53 to any desired position.

It is appreciated that valves which function similarly to those represented by the openings 21 and corresponding spheres 19 depicted in FIG. 3 may also be utilized with the above-described embodiments of the present invention. Further, the above-described embodiments of the present invention are not restricted to NMR scanners; but, may entail any variety of apparatus into which an object is positioned for examination purposes.

The present invention also entails methods corresponding to the operations of the preferred embodiments of the apparatus of the present invention described above.

While the invention has been described in its preferred embodiments, it is to be understood that the words which have been used are words of description rather than limitation, and that changes within the purview of the appended claims may be made without departing from the true scope of spirit of the invention in its broader aspects.

What is claimed is:

1. An examination apparatus having an examination region and a surface extending into said region, said examination apparatus further comprising:
    (a) means for examining an object in said examination region;
    (b) support means for supporting said object;
    (c) fluid pressure supply means for providing a source of pressurized fluid;
    (d) valve means protruding from said surface and operable to communicate pressurized fluid from said fluid pressure supply means to a location beneath said support means when said support means contacts said valve means;
    (e) a first sprocket and a second sprocket spacedly positioned adjacent said surface and belt means disposed around and cooperating with said first and second sprockets; and
    (f) said support means including engagement means thereon adapted to be engaged by said belt means for selectively positioning said support means relative to said examination region.

2. The apparatus claimed in claim 1, wherein said first sprocket is driven with a motor for automated positioning of said support means, said motor being remotely situated from said examination region.

3. The apparatus claimed in claim 1, wherein said means for examining an object is an NMR scanner.

4. The apparatus of claim 1 wherein said surface further comprises guiding means for guiding said support means along said surface; and wherein said support means comprises means for cooperating with said guiding means.

5. The apparatus of claim 4 wherein said guiding means comprises a first and a second track disposed along said surface so that said valve means are disposed between said tracks;
    wherein said support means comprises a support having a side and a bottom surface with grooves therein engaging said tracks; and
    wherein said engagement means comprises a third sprocket on said side of said support for engagement with said belt means, said third sprocket being selectively rotatable.

6. The apparatus of claim 5 further including means, coupled to said first sprocket, for selectively driving said first sprocket in a first and a second direction.

7. The apparatus of claim 1 wherein said support means comprises a patient bed.

8. A method of selectively positioning an object in an examination apparatus having an examination region and a surface extending into said region, comprising the steps of:
    (a) disposing a support on said surface;
    (b) disposing an object for examination on said support;
    (c) supplying, through valve means in said surface, fluid pressure beneath said support to support said support on a fluidic cushion, said valve means being operable when contacted by said support; and
    (d) moving said support along guide means on said surface relative to said examination region by belt means, said belt means being disposed around and cooperative with a first sprocket and second sprocket spacedly positioned on said surface, and said belt means engaging said support to selectively position said support relative to said region.

9. The method claimed in claim 8, wherein said movement of said support is accomplished by driving said first sprocket with a motor.

10. The method claimed in claim 8, including the additional step of examining said object by means of an NMR scanner apparatus.

11. An NMR scanning apparatus, comprising:
(a) a support platform having an examination region and a surface extending into said region;
(b) NMR scanning means for examining an object by NMR techniques, said NMR scanning means generating a substantially uniform magnetic field in said examination region;
(c) transport means for supporting said object;
(d) means for movably supporting said transport means for movement relative to said support platform; and
(e) said means for movably supporting said transport means including fluid-pressure supply means, remotely situated relative to said examination region, for providing a fluidic cushion between said surface and said transport means, thereby facilitating support of said transport means for movement relative to said support platform.

12. The NMR scanning apparatus as claimed in claim 11, wherein said fluid-pressure supply means includes valve means operatively associated with said surface and selectively operable to provide said fluidic cushion beneath said transport means during movement of said transport means relative to said support platform.

13. The NMR scanning apparatus as claimed in claim 12, wherein said valve means comprises openings in said surface, and rotatable members mounted and protruding beyond said surface, said rotatable members being adapted for movement between a seated position in which said rotatable members close said openings and a depressed position in which said rotatable members permit fluid flow through said openings from said fluid-pressure supply means.

14. The NMR scanning apparatus as claimed in claim 13, wherein said rotatable members are mounted for movement into said depressed position upon contact with said transport means during movement of said transport means relative to said support platform.

15. The NMR scanning apparatus as claimed in claim 11, further including positioning means operatively associated with said surface and said transport means for selectively positioning said transport means relative to said examination region.

16. The NMR scanning apparatus as claimed in claim 15, wherein said positioning means includes movable belt means and engagement means on said transport means, said belt means being associated with said surface for cooperative engagement with said engagement means to move said transport means relative to said surface.

17. The NMR scanning apparatus as claimed in claim 16, wherein said positioning means further includes a motor for driving said belt means for automated positioning of said transport means.

18. The NMR scanning apparatus as claimed in claim 15, wherein said positioning means includes belt means associated with said surface and selectively rotatable sprocket means on said transport means for cooperative engagement with said belt means.

19. The NMR scanning apparatus as claimed in claim 11, further including pedestal means adjacent said support platform and having a pedestal surface for supporting said transport means; adjustment means for vertically adjusting said pedestal surface relative to said surface of said support platform so that said pedestal surface is in register with said surface of said support platform; and pedestal support means associated with said pedestal means for movably supporting said transport means for movement relative to said pedestal surface.

20. The NMR scanning apparatus of claim 19 wherein said pedestal support means includes pedestal fluid pressure supply means for providing a fluidic cushion between said pedestal surface and said transport means to thereby facilitate support of said transport means for movement relative to said pedestal surface.

21. The NMR scanning apparatus of claim 20 wherein said fluid pressure supply means for providing a fluidic cushion between said surface of said support platform and said transport means includes first valve means operatively associated with said surface of said support platform and wherein said pedestal fluid pressure supply means includes second valve means operatively associated with said pedestal surface, said first and second valve means being selectively operable to provide said fluidic cushions, respectively, beneath said transport means during movement of said transport means relative to said support platform and beneath said transport means during movement of said transport means relative to said pedestal surface.

22. The NMR scanning apparatus of claim 21 wherein said first valve means comprises first openings in said surface of said support platform and first rotatable members mounted in said first openings and protruding beyond said surface of said support platform, and wherein said second valve means comprises second openings in said pedestal surface and second rotatable members mounted in said second openings and protruding beyond said pedestal surface, each of said first and second rotatable members being adapted for movement between a seated position in which said rotatable members close said openings and a depressed position in which said rotatable members permit fluid to flow through said openings.

23. The NMR scanning apparatus as claimed in claim 22 wherein said first and second rotatable members are mounted for movement into said depressed positions upon contact with said transport means during movement of said transport means.

24. The NMR scanning apparatus as claimed in claim 20, further including first positioning means operatively associated with said surface of said support platform and said transport means for selectively positioning said transport means relative to said examination region, and second positioning means operatively associated with said pedestal surface and said transport means for selectively positioning said transport means relative to said pedestal means.

25. The NMR scanning apparatus as claimed in claim 24 wherein said first and second positioning means include engagement means on said transport means and first and second movable belt means, said first movable belt means being associated with said surface of said support platform for cooperative engagement with said engagement means to move said transport means relative to said surface of said support platform and said second movable belt means being associated with said pedestal surface for cooperative engagement with said engagement means to move said transport means relative to said pedestal surface.

26. The NMR scanning apparatus of claim 20 further including guide means on said surface of said support platform and on said pedestal surface, said guide means being operatively associated with said transport means for alignment of said transport means during movement thereof.

27. A method of conducting an examination of an object, said method comprising the steps of:
 (a) providing a support platform having an examination region and a surface extending into said examination region;
 (b) providing NMR scanning means for examining an object by NMR techniques, said NMR scanning means being capable of generating a substantially uniform magnetic field in said examination region;
 (c) placing an object for examination on a transport means;
 (d) supplying, from a source remotely situated from said examination region, fluid pressure beneath said transport means to support said transport means on a fluidic cushion between said surface and said transport means;
 (e) moving said transport means relative to said surface so as to position at least a portion of said object in said examination region; and
 (f) examining said object by NMR techniques.

28. The method claimed in claim 27, wherein said fluid pressure is supplied through valve means in said surface, said valve means being operable when engaged by said transport means.

29. The method claimed in claim 27, further including the steps of: (i) providing pedestal means adjacent said support platform and having a pedestal surface for supporting said transport means, said pedestal surface being vertically adjustable relative to said surface of said support platform; (ii) prior to said step (c), supporting said transport means on said pedestal means; and (iii) after said step (c) and prior to said steps (e) and (f), vertically adjusting said pedestal surface relative to said surface of said support platform so that said pedestal surface is in register with said surface of said support platform, and then moving said transport means from said pedestal means to said support platform.

30. The method of claim 29 wherein said step of moving said transport means from said pedestal means to said support platform comprises the steps of supplying fluid pressure beneath said transport means to support said transport means on a fluidic cushion between said pedestal surface and said transport means.

31. The method of claim 30 wherein said steps of supplying fluid pressure beneath said transport means comprises supplying fluid pressure through valve means in said pedestal surface and in said surface of said support platform, said valve means being operable when engaged by said transport means.

* * * * *

UNITED STATES PATENT AND TRADEMARK OFFICE
CERTIFICATE OF CORRECTION

PATENT NO. : 4,805,626

DATED : February 21, 1989

INVENTOR(S) : DiMassimo et al.

It is certified that error appears in the above-identified patent and that said Letters Patent is hereby corrected as shown below:

Column 2, line 28, delete "or", and insert therefor --for-.
         line 62, delete "alone", and insert therefor --along--.

Column 5, line 27, delete "the" (second occurrence) and insert therefor --be--.

Column 12, after line 30, insert the following claim (original Claim 55): --32. The NMR scanning apparatus as claimed in Claim 11, wherein said surface includes guide means operatively associated with said transport means for alignment of said transport means during movement thereof.--

Signed and Sealed this

Twelfth Day of September, 1989

Attest:

DONALD J. QUIGG

Attesting Officer

Commissioner of Patents and Trademarks